(12) United States Patent
Nakatani et al.

(10) Patent No.: US 9,394,321 B2
(45) Date of Patent: Jul. 19, 2016

(54) MODIFYING AGENT, METHOD FOR PRODUCING MODIFIED CONJUGATED DIENE POLYMER USING MODIFYING AGENT, AND MODIFIED CONJUGATED DIENE POLYMER

(71) Applicant: BRIDGESTONE CORPORATION, Tokyo (JP)

(72) Inventors: Kenji Nakatani, Tokyo (JP); Yuki Itoh, Tokyo (JP)

(73) Assignee: BRIDGESTONE CORPORATION, Tokyo (JP)

( * ) Notice: Subject to any disclaimer, the term of this patent is extended or adjusted under 35 U.S.C. 154(b) by 0 days.

(21) Appl. No.: 14/547,316

(22) Filed: Nov. 19, 2014

(65) Prior Publication Data
US 2015/0073166 A1 Mar. 12, 2015

Related U.S. Application Data

(62) Division of application No. 13/394,741, filed as application No. PCT/JP2010/065555 on Sep. 9, 2010, now abandoned.

(30) Foreign Application Priority Data

Sep. 9, 2009 (JP) ................................. 2009-208656
Sep. 9, 2009 (JP) ................................. 2009-208657

(51) Int. Cl.
*C08C 19/25* (2006.01)
*C07F 7/18* (2006.01)
*B60C 1/00* (2006.01)
*C08L 15/00* (2006.01)
*C08C 19/44* (2006.01)

(52) U.S. Cl.
CPC ............ *C07F 7/1888* (2013.01); *B60C 1/0016* (2013.04); *C07F 7/1876* (2013.01); *C08C 19/25* (2013.01); *C08C 19/44* (2013.01); *C08L 15/00* (2013.01)

(58) Field of Classification Search
None
See application file for complete search history.

(56) References Cited

U.S. PATENT DOCUMENTS

| | | | |
|---|---|---|---|
| 3,595,895 A | 7/1971 | Bush et al. | |
| 5,932,651 A | 8/1999 | Liles et al. | |
| 2005/0159554 A1 | 7/2005 | Endou et al. | |
| 2008/0103261 A1* | 5/2008 | Tanaka et al. | 525/331.9 |
| 2010/0016500 A1 | 1/2010 | Sone et al. | |

FOREIGN PATENT DOCUMENTS

| | | |
|---|---|---|
| DE | 4436077 | 4/1996 |
| EP | 2 130 841 A1 | 12/2009 |
| EP | 2 266 819 A1 | 12/2010 |
| JP | 8-165389 A | 6/1996 |
| JP | 9-169823 A | 6/1997 |
| JP | 2001-163982 A | 6/2001 |
| JP | 2007-308646 | * 11/2007 |
| JP | 2008-106118 A | 5/2008 |
| JP | 2008-202054 A | 9/2008 |
| JP | 2009-242788 A | 10/2009 |
| WO | 2008/123163 A1 | 10/2008 |

OTHER PUBLICATIONS

Kruger, Zeitschrift fur Anorganische and Allgemein Chemie. Band 338, 1965, p. 113-120.*
Translation of JP 2007-308646 (2007).*
Extended European Search Report issued Jul. 12, 2013 in corresponding European Patent Application No. 10815428.7.
Krüger Zeitschrift Fur anorganische und allgemeine Chemie, vol. 338, Issue 3-4, pp. 113-120, Aug. 1965.
Translation of DE 4436077 (Apr. 1996).

* cited by examiner

*Primary Examiner* — Robert C Boyle
(74) *Attorney, Agent, or Firm* — Sughrue Mion, PLLC

(57) ABSTRACT

Provided are a modifying agent obtained by subjecting a silicon-containing compound having a protected primary amino group and at least two hydrolyzable groups to complete condensation, a method of producing a modified conjugated diene-based polymer, a modified conjugated diene-based polymer obtained by the production method, a rubber composition using the polymer, and a pneumatic tire. The modified conjugated diene-based polymer has excellent low heat generating property and abrasion resistance, and the rubber composition is obtained by using the modified conjugated diene-based polymer and the pneumatic tire is obtained by using the rubber composition.

3 Claims, No Drawings

MODIFYING AGENT, METHOD FOR PRODUCING MODIFIED CONJUGATED DIENE POLYMER USING MODIFYING AGENT, AND MODIFIED CONJUGATED DIENE POLYMER

This is a Divisional of application Ser. No. 13/394,741 filed May 14, 2012, which is a 371 of PCT/JP/2010/065555 filed Sep. 9, 2010, which claims benefit of priority from JP 2009-208656 and JP 2009-208657, both filed Sep. 9, 2009; the disclosures of which are incorporated herein by reference in their entirety.

TECHNICAL FIELD

The present invention relates to a modifying agent, a method of producing a modified conjugated diene-based polymer using the modifying agent, and the modified conjugated diene-based polymer, and a rubber composition using the polymer and a pneumatic tire using the rubber composition.

BACKGROUND ART

A large number of technologies concerning a modified rubber for a rubber composition using silica or carbon black as a filler have been conventionally developed in order that a rubber composition having low heat generating property may be obtained. Of those, in particular, the following method has been proposed as an effective method (see, for example, Patent Literature 1 or 2). A polymerization active site of a conjugated diene-based polymer obtained by anionic polymerization involving using an organic lithium is modified with an alkoxysilane derivative containing a functional group that interacts with a filler.

Compounding a reinforcing filler into a rubber composition using a modified polymer obtained by the production method can secure low heat generating property. However, abrasion resistance when silica is applied to the reinforcing filler has still been insufficient.

In recent years, however, a request for a reduction in the fuel consumption of an automobile has started to become more and more stringent in relation to a social demand for energy savings and a global trend toward carbon dioxide emission control in association with the growth of interests in environmental problems. Accordingly, there have been growing requests for improvements in the low heat generating property and abrasion resistance of a rubber composition, and hence additional development has been requested.

CITATION LIST

Patent Literature

[PTL 1] JP 06-57767 B
[PTL 2] WO 03/029299 A1

SUMMARY OF INVENTION

Technical Problem

In view of such circumstances, a problem to be solved by the present invention is to provide a modifying agent with which a modified conjugated diene-based polymer excellent in low heat generating property and abrasion resistance can be obtained, and an object of the present invention is to provide a modified conjugated diene-based polymer using the modifying agent, a rubber composition using the polymer, and a pneumatic tire using the rubber composition.

Solution to Problem

The inventors of the present invention have made extensive studies to achieve the object, and as a result, have found that the object can be achieved by using a modifying agent obtained by condensing a silicon-containing compound having a specific amino group that is protected and a specific hydrolyzable group. The present invention has been completed on the basis of such finding.

That is, the present invention provides:
(1) a modifying agent obtained by subjecting a silicon-containing compound having a protected primary amino group and at least two hydrolyzable groups to complete condensation;
(2) a method of producing a modified conjugated diene-based polymer, comprising: a modifying step of causing the modifying agent according to the above-mentioned item (1) to react with an active site of a conjugated diene-based polymer having the active site to modify the polymer; and a deprotecting step to be performed after completion of the modifying step;
(3) a modified conjugated diene-based polymer obtained by the production method according to the above-mentioned item (2);
(4) a rubber composition, comprising the modified conjugated diene-based polymer according to the above-mentioned item (3); and
(5) a pneumatic tire obtained by using the rubber composition according to the above-mentioned item (4).

Advantageous Effects of the Invention

According to the present invention, there can be provided a modified conjugated diene-based polymer excellent in low heat generating property and abrasion resistance, a rubber composition using the modified conjugated diene-based polymer, and a pneumatic tire using the rubber composition.

In addition, according to the present invention, there can be provided a modified conjugated diene-based polymer that does not generate any volatile organic compound (VOC).

DESCRIPTION OF EMBODIMENTS

A modifying agent of the present invention is characterized by being obtained by subjecting a silicon-containing compound having a protected primary amino group and at least two hydrolyzable groups to complete condensation.

The hydrolyzable groups are each preferably a hydrolyzable group that forms a silanol group together with at least two silicon atoms by hydrolysis. Here, the term "complete condensation" means that all monomers of the silicon-containing compound in the modifying agent are condensed and hence no monomer of the silicon-containing compound exists in the modifying agent. The silicon-containing compound needs to have at least two hydrolyzable groups each of which forms a silanol group together with a silicon atom in order that the silicon-containing compound may be hydrolyzed and completely condensed.

The modifying agent of the present invention may be obtained by the condensation of compounds of the same kind, or may be obtained by the condensation of two or more kinds of dissimilar compounds.

Each of the hydrolyzable functional groups is a functional group capable of chemically reacting with an active site of a conjugated diene-based polymer, and is preferably a hydrocarbyloxy group or a halogen atom, more preferably a group selected from the group consisting of an alkoxy group having 1 to 12 carbon atoms, a phenoxy group and a benzyloxy group, or a halogen atom, still more preferably an alkoxy group having 1 to 20 carbon atoms, particularly preferably an alkoxy group having 1 to 12 carbon atoms. A methoxy group, an ethoxy group, a propyloxy group, an isopropyloxy group, an n-butoxy group, and a tert-butoxy group can be given as specific examples of the alkoxy group having 1 to 20 carbon atoms. The halogen atom is preferably a chlorine atom, a bromine atom, or a fluorine atom.

The modifying agent of the present invention is preferably a compound represented by the following general formula (1) or (2).

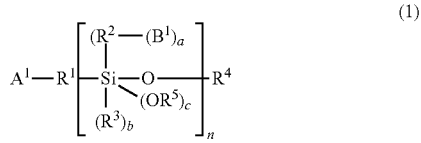
(1)

(In the formula, $R^1$ and $R^2$ each represent a divalent aliphatic hydrocarbon group having 1 to 20 carbon atoms, a divalent aromatic hydrocarbon group having 6 to 18 carbon atoms, or a single bond, and may be identical to or different from each other, $R^3$, $R^4$, and $R^5$ each represent a monovalent aliphatic hydrocarbon group having 1 to 20 carbon atoms or a monovalent aromatic hydrocarbon group having 6 to 18 carbon atoms, and may be identical to or different from one another, $A^1$ represents a group for bonding the modifying agent and a conjugated diene-based polymer by adding to, or substituting for, an active site of the conjugated diene-based polymer, $B^1$ represents a primary amino group protected with a hydrolyzable protective group, $a+b+c=2$, a represents 1 to 2, b represents 0 to 1, and n represents 2 to 20.)

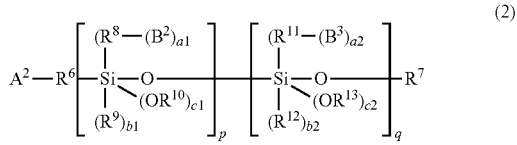
(2)

(In the formula, $R^6$, $R^8$, and $R^{11}$ each represent a divalent aliphatic hydrocarbon group having 1 to 20 carbon atoms, a divalent aromatic hydrocarbon group having 6 to 18 carbon atoms, or a single bond, and may be identical to or different from each other, $R^7$, $R^9$, $R^{10}$, $R^{12}$, and $R^{13}$ each represent a monovalent aliphatic hydrocarbon group having 1 to 20 carbon atoms or a monovalent aromatic hydrocarbon group having 6 to 18 carbon atoms, and may be identical to or different from one another, $A^2$ represents a group for bonding the modifying agent and a conjugated diene-based polymer by adding to, or substituting for, an active site of the conjugated diene-based polymer, $B^2$ represents a primary amino group protected with a hydrolyzable protective group, $B^3$ represents a linear, branched, alicyclic, or aromatic, monovalent hydrocarbon group having 1 to 30 carbon atoms and having a functional group selected from the group consisting of an isocyanate group, a thioisocyanate group, an imine residue, an amide group, a cyclic secondary amino group, an onium salt residue of a cyclic secondary amine, a non-cyclic secondary amino group, an onium salt residue of a non-cyclic secondary amine, an isocyanuric acid triester residue, a cyclic tertiary amino group, a non-cyclic tertiary amino group, a nitrile group, a pyridine residue, an onium salt residue of a cyclic tertiary amine, and an onium salt residue of a non-cyclic tertiary amine, or a linear, branched, alicyclic, or aromatic, monovalent hydrocarbon group having 1 to 30 carbon atoms which may contain at least one kind of heteroatom selected from an oxygen atom, a sulfur atom, and a phosphorus atom, $a1+b1+c1=2$, a1 represents 1 to 2, b1 represents 0 to 1, $a2+b2+c2=2$, a2, b2, and c2 each represent 0 to 2, and p and q each independently represent 1 to 10.)

The general formula (2) is represented as $A^2$-$R^6$—$X_p$—$Y_q$—$R^7$ when X and Y are defined as represented by the following general formulae (2a) and (2b). The general formula (2) has only to be such that a total of p X's and a total of q Y's exist, and the order in which X's and Y's are arranged is not limited. The order of X and Y may be inverted like $A^2$-$R^6$—$Y_q$—$X_p$—$R^7$. In addition, the "$X_p$" part in the general formula (2) may be such that the p X's are not continuous. Similarly, the "$Y_q$" part may be such that the q Y's are not continuous. X's and Y's may be alternately arranged, or X's and Y's may be arranged at random like, for example, —XXYXYY—.

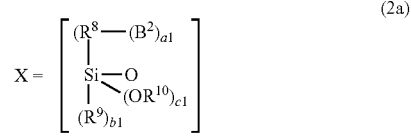
(2a)

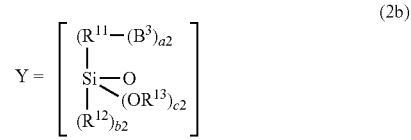
(2b)

In the general formulae (1) and (2), $A^1$ and $A^2$ each represent preferably a hydrolyzable group, more preferably a hydrocarbyloxy group or a halogen atom. The hydrocarbyloxy group is more preferably an alkoxy group having 1 to 12 carbon atoms, a phenoxy group, or a benzyloxy group. $R^1$ and $R^6$ each preferably represent a single bond. $R^2$ and $R^8$ each preferably represent a divalent aliphatic hydrocarbon group having 1 to 20 carbon atoms or a divalent aromatic hydrocarbon group having 6 to 18 carbon atoms.

In addition, that $R^1$ in the general formula (1) represents a single bond means that $A^1$ and Si are directly bonded to each other through the single bond, that $R^6$ in the general formula (2) represents a single bond means that $A^2$ and Si are directly bonded to each other through the single bond, and the same holds true for any other case.

Described here is an example of the modifying agent in the present invention obtained by hydrolyzing the silicon-containing compound having a protected primary amino group and at least two hydrolyzable groups to condensate the compound via a silanol group, in particular, to completely condensate the compound.

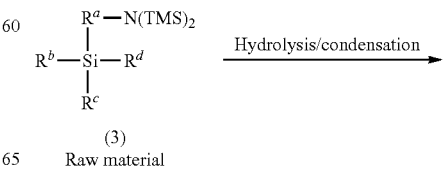
(3)
Raw material

-continued

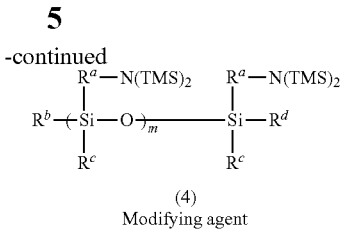

(4)
Modifying agent

The formula (3) represents a raw material for the modifying agent and the formula (4) represents the modifying agent to be used in the step of modifying a diene-based copolymer, the modifying agent being obtained by hydrolyzing the raw material to completely condensate the raw material.
(In the formulae (3) and (4), $R^a$ represents a divalent hydrocarbon group having 1 to 20 carbon atoms, $R^b$ and $R^d$ each represent a hydrolyzable group (preferably a hydrocarbyloxy group or a halogen atom), $R^c$ represents a hydrolyzable group (preferably a hydrocarbyloxy group or a halogen atom) or a hydrocarbyl group, TMS represents a trimethylsilyl group as a protective group for a primary amino group, and m represents 2 to 20.)

The formula (4) is obtained by the condensation of disilanol compounds and condensation with a monosilanol compound for sealing an end of the resultant, and m represents the condensation degree of the formula, which is preferably 2 to 20, particularly preferably 2 to 10.

In addition, the active site at an end of the polymer (conjugated diene-based polymer) can react with any one of $R^b$ and $R^d$ of the modifying agent.

The silicon-containing compound represented by the formula (3) is, for example, a hydrocarbyloxysilane compound having a protected primary amino group having, as protective groups, two trialkylsilyl groups each represented by —$SiR^e R^f R^g$ (where $R^e$, $R^f$, and $R^g$ each independently represent an alkyl group having 1 to 12 carbon atoms, preferably a methyl group, an ethyl group, a propyl group, or a butyl group). Specific examples of the hydrocarbyloxysilane compound having a protected primary amino group preferably include N,N-bis(trimethylsilyl)aminopropyltrimethoxysilane, N,N-bis(trimethylsilyl)aminopropylmethyltriethoxysilane, N,N-bis(trimethylsilyl)aminopropylmethyldimethoxysilane, N,N-bis(trimethylsilyl)aminopropylmethyldiethoxysilane, N,N-bis(trimethylsilyl)aminoethylmethyldimethoxysilane, and N,N-bis(trimethylsilyl)aminoethylmethyldiethoxysilane. Of those, N,N-bis(trimethylsilyl)aminopropylmethyldimethoxysilane and N,N-bis(trimethylsilyl)aminopropylmethyldiethoxysilane are particularly preferred.

Examples of the compounds which has a halogen atom include N,N-bis(trimethylsilyl)aminopropylmethylmethoxychlorosilane, N,N-bis(trimethylsilyl)aminopropylmethylethoxychlorosilane, N,N-bis(trimethylsilyl)aminoethylmethylmethoxychlorosilane, and N,N-bis(trimethylsilyl)aminoethylmethylethoxychlorosilane.

N,N-bis(trimethylsilyl)aminopropyltrimethoxysilane, N,N-bis(trimethylsilyl)aminopropylmethyltriethoxysilane, N,N-bis(trimethylsilyl)aminopropylmethyldimethoxysilane, N,N-bis(trimethylsilyl)aminopropylmethyldiethoxysilane, and 1-trimethylsilyl-2-ethoxymethyl-1-aza-2-cyclopentane are preferred, and complete condensation products thereof are utilized as a modifying agent. Those modifying agents may be used alone or in combination of two or more kinds thereof. However, partial condensation products are utilized as a modifying agent but with little effect.

In this case, the partial condensation product is a compound prepared by converting a part (not all) of SiOR in the modifying agent to a SiOSi bond by condensation.

The hydrocarbyloxysilane compound having a protected primary amino group is preferred, and the introduction of the primary amino group into a molecular chain end of a modified conjugated diene-based polymer significantly improves the low heat generating property of a rubber composition into which the modified conjugated diene-based polymer is compounded.

In addition, the use of a complete condensation product as a modifying agent can achieve, for example, an improvement in abrasion resistance as compared with a conventional modifying agent because the use improves, in particular, an affinity between silica and the polymer at a modifying group portion that exerts a reinforcing effect.

When the modifying agent obtained by condensing the silicon-containing compound having a protected primary amino group and at least two hydrolyzable groups is used in the production of a modified conjugated diene-based polymer of the present invention, the number of functional groups per unit modified conjugated diene-based polymer increases. Accordingly, a rubber composition having an increased affinity for a filler such as silica or carbon black, and excellent in low heat generating property and abrasion resistance is obtained. As a silanol group produced by the hydrolysis of a hydrolyzable functional group site has higher reactivity with silica, a rubber composition more excellent in low heat generating property and abrasion resistance is obtained.

In addition, a method of producing the modified conjugated diene-based polymer of the present invention is characterized by comprising: a modifying step of causing the modifying agent to react with an active site of the conjugated diene-based polymer having the active site to modify the polymer; and a deprotecting step to be performed after the completion of the modifying step. Through the deprotecting step, a protective group leaves from the protected primary amino group so that a primary amino group may be produced.

The production method of the present invention preferably further comprises a hydrolyzing step between the modifying step and the deprotecting step, or after the deprotecting step or simultaneously with the deprotecting step. The method preferably comprises (a) the modifying step of causing the modifying agent to react with an active site of the conjugated diene-based polymer having the active site to modify the polymer and (b) a hydrolyzing step to be performed after the completion of the modifying step. Through such step, a silanol group is provided for a molecular chain end of the modified conjugated diene-based polymer of the present invention.

In the present invention, the hydrolyzable group that produces a silanol group by hydrolysis is an alkoxysilane group or a halogen atom, and is more preferably such that 10% or more of the compound produces a silanol group by hydrolysis in terms of an effect of the present invention. The protective group of the protected primary amino group is preferably a hydrolyzable protective group because the deprotecting step and the hydrolyzing step can be simultaneously performed.

It should be noted that the term "conjugated diene-based polymer" in the present invention comprehends a conjugated diene polymer and a conjugated diene copolymer.

When the characteristic group that produces a silanol group by hydrolysis reacts with a reinforcing filler, in particular, silica, the group needs to turn into a silanol group by the reaction. However, when the group is a silanol group from the start, the following large effects are exerted. Reactivity with silica becomes higher, the dispersibility of silica in a rubber composition is improved, and the low heat generating property of the rubber composition is improved. Further, the case where the characteristic group that produces a silanol group by hydrolysis is an alkoxy group is preferred in terms of a working environment because a volatile organic compound (VOC, especially an alcohol) is generated but no silanol group is generated.

A conjugated diene monomer to be used in the modified conjugated diene-based polymer in the method of producing the modified conjugated diene-based polymer of the present invention is preferably, for example, 1,3-butadiene, isoprene, 1,3-pentadiene, 2,3-dimethyl-1,3-butadiene, 2-phenyl-1,3-butadiene, or 1,3-hexadiene. They may be used alone or in combination of two or more kinds thereof. Of those, one kind selected from 1,3-butadiene, isoprene, and 2,3-dimethyl-1,3-butadiene is more preferred, and 1,3-butadiene is particularly preferred.

Further, an aromatic vinyl monomer to be used in the conjugated diene-based polymer is, for example, styrene, α-methylstyrene, 1-vinylnaphthalene, 3-vinyltoluene, ethylvinylbenzene, divinylbenzene, 4-cyclohexylstyrene, and 2,4,6-trimethylstyrene. They may be used alone or in combination of two or more kinds thereof. Of those, styrene is particularly preferred.

The conjugated diene-based polymer in the method of producing the modified conjugated diene-based polymer of the present invention is preferably a polybutadiene, a polyisoprene, a butadiene-isoprene copolymer, a styrene-butadiene copolymer, a styrene-isoprene copolymer, or a styrene-isoprene-butadiene terpolymer. Of those, the polybutadiene and the styrene-butadiene copolymer are particularly preferred.

The method of producing the modified conjugated diene-based polymer of the present invention is described in detail. In order that the active site of the conjugated diene-based polymer and an organosilane compound in the modifying step of the production method of the present invention may be caused to react with each other, the conjugated diene-based polymer to be used is preferably such that at least 10% of its polymer chains have living property or pseudo-living property. A polymerization reaction having such living property is preferably anionic polymerization or coordination anionic polymerization. Of those, the anionic polymerization is particularly preferred because the polymerization does not require the preliminary modifying step.

Although the active site of the conjugated diene-based polymer in the modifying step of the production method of the present invention may be any one of the active site (active site at a molecular chain end) of the conjugated diene-based polymer, an active site in its main chain, and an active site in a side chain thereof, the active site of the conjugated diene-based polymer is preferably an active end when the active site is obtained by anionic polymerization or coordination anionic polymerization.

The production method of the present invention is preferably such that the conjugated diene-based polymer having an active site is obtained by subjecting a conjugated diene compound alone, or the conjugated diene compound and an aromatic vinyl compound, to anionic polymerization with an organic alkali metal compound as a polymerization initiator.

An organic lithium compound is preferably used as the organic alkali metal compound to be used as the initiator for the anionic polymerization described above. No particular limitation is imposed on the organic lithium compound, and a hydrocarbyllithium and a lithium amide compound are preferably used. When the hydrocarbyllithium is used, a conjugated diene polymer and a conjugated diene-based polymer each having a hydrocarbyl group at a polymerization-initiating end and a polymerization active site at the other end are produced. Further, when the lithium amide compound is used, a conjugated diene polymer and a conjugated diene-based polymer each having a nitrogen-containing group at a polymerization-initiating end and a polymerization active site at the other end are produced.

The hydrocarbyllithium is preferably a compound having a hydrocarbyl group having 2 to 20 carbon atoms. Examples thereof include ethyllithium, n-propyllithium, isopropyllithium, n-butyllithium, sec-butyllithium, tert-octyllithium, n-decyllithium, phenyllithium, 2-naphthyllithium, 2-butylphenyllithium, 4-phenyl-butyllithium, cyclohexyllithium, cyclopentyllithium, and a reaction product of diisopropenylbenzene with butyllithium. Of those, n-butyllithium is particularly suited.

On the other hand, the lithium amide compound includes, for example, lithium hexamethyleneimide, lithium pyrrolidide, lithium piperidide, lithium heptamethyleneimide, lithium dodecamethyleneimide, lithium dimethylamide, lithium diethylamide, lithiumdibutylamide, lithiumdipropylamide, lithiumdiheptylamide, lithium dihexylamide, lithium dioctylamide, lithium di-2-ethylhexylamide, lithium didecylamide, lithium-N-methylpiperazide, lithium ethylpropylamide, lithium ethylbutylamide, lithium ethylbenzylamide, and lithium methylphenethylamide. Of those, cyclic lithium amides such as lithium hexamethyleneimide, lithium pyrrolidide, lithium piperidide, lithium heptamethyleneimide, and lithium dodecamethyleneimide are preferred in terms of interaction with carbon black and polymerization initiating ability. Particularly suited are lithium hexamethyleneimide and lithium pyrrolidide.

Generally, those lithium amide compounds for use in polymerization may be prepared in advance from a secondary amine and a lithium compound. Alternatively, the amide compounds may also be prepared in the polymerization system (in-situ). The usage of the polymerization initiator is preferably selected in the range of 0.2 to 20 mmol per 100 g of the monomer.

No particular limitation is imposed on the method of producing a conjugated diene-based polymer through anionic polymerization employing the organic lithium compound serving as a polymerization initiator, and any conventionally known methods may be employed.

Specifically, in an organic solvent which is inert to the reaction such as a hydrocarbon-based solvent including aliphatic, alicyclic, and aromatic hydrocarbon compounds, a conjugated diene monomer or a mixture of a conjugated diene monomer and an aromatic vinyl monomer is anionically polymerized in the presence of the lithium compound serving as a polymerization initiator and an optional randomizer, thereby producing a conjugated diene-based polymer of interest having an active site.

In addition, in the case where the organic lithium compound is used as the polymerization initiator, not only the conjugated diene polymer having an active site but also the conjugated diene-aromatic vinyl copolymer having an active site can be obtained with higher efficiency than that in the case where the catalyst containing a lanthanum series rare earth element compound is used.

The hydrocarbon-based solvent is preferably a hydrocarbon having 3 to 8 carbon atoms. Examples thereof include propane, n-butane, isobutane, n-pentane, isopentane, n-hexane, cyclohexane, propene, 1-butene, isobutene, trans-2-butene, cis-2-butene, 1-pentene, 2-pentene, 1-hexene, 2-hexene, benzene, toluene, xylene, and ethylbenzene. They may be used alone or in combination of two or more kinds thereof.

In addition, a monomer concentration in the solvent is preferably 5 to 50 mass %, more preferably 10 to 30 mass %. It should be noted that, when copolymerization is carried out with the conjugated diene monomer and the aromatic vinyl monomer, the content of the aromatic vinyl monomer in a mixture of the loaded monomers preferably falls within the range of 55 mass % or less.

Further, the randomizer, which may be used in accordance with needs, is a compound which is capable of controlling a microstructure of a conjugated diene-based polymer such as increasing 1,2-bonds of the butadiene moieties in a styrene-butadiene copolymer or 3,4-bonds in an isoprene polymer or controlling the monomer unit composition distribution in a conjugated diene-aromatic vinyl copolymer such as randomizing butadiene units and styrene units in a styrene-butadiene copolymer. No particular limitation is imposed on the type of randomizer, and any of known compounds conventionally used as a randomizer may appropriately employed. Specific examples of the randomizer include ethers and tertiary amines such as dimethoxybenzene, tetrahydrofuran, dimethoxyethane, diethylene glycol dibutyl ether, diethylene glycol dimethyl ether, 2,2-bis(2-tetrahydrofuryl)-propane, triethylamine, pyridine, N-methylmorpholine, N,N,N',N'-tetramethylethylenediamine, and 1,2-piperidinoethane. Further, potassium salts such as potassium t-amylate and potassium t-butoxide and sodium salts such as sodium t-amylate may also be employed.

Those randomizers may be used alone or in combination of two or more kinds thereof. The usage of the randomizer is preferably selected in the range of 0.01 to 1000 mole equivalents per mole of the lithium compound.

The temperature of the polymerization reaction is preferably selected in the range of 0 to 150° C., more preferably 20 to 130° C. The polymerization reaction may be carried out under generated pressure, but generally desirably performed under such pressure that the monomer is maintained virtually as a liquid phase. That is, a higher pressure may be employed in accordance with needs, although depending on the individual substances to be polymerized, polymerization solvent, and polymerization temperature. Such pressure may be obtained through an appropriate method such as applying pressure to a reactor by use of gas inert to the polymerization reaction.

In the anionic polymerization, all raw materials involved in the polymerization such as the polymerization initiator, the solvent, and the monomer are desirably used after reaction inhibitors such as water, oxygen, carbon dioxide, and a protonic compound have been removed from the raw materials.

The polymerization reaction may be performed according to any one of a batch mode and a continuous mode.

Thus, the conjugated diene-based polymer having an active site is obtained.

In the modifying step of the method of producing the modified conjugated diene-based polymer of the present invention, the modifying agent is added to the conjugated diene-based polymer having an active site obtained as described above preferably in a stoichiometric amount with respect to the active site of the conjugated diene-based polymer or an amount in excess thereof so as to be caused to react with the active site bonded to the polymer.

The modifying step of the present invention is typically performed under the same temperature and pressure conditions as those of the polymerization reaction.

The amino group derived from the modifying agent of the modified conjugated diene-based polymer of the present invention is preferably deprotected so as to be converted into a primary amino group. The following procedure is employed in the deprotecting step of performing a deprotection treatment.

That is, the protected amino group is converted into a free amino group by the hydrolysis of a silyl protective group on the group. Subjecting the resultant to a desolvation treatment provides a dry polymer having a primary amino group. It should be noted that the deprotection treatment of the protected primary amino group derived from the modifying agent can be performed as required at any one of the stages ranging from a stage involving a condensation treatment to be described later to the stage at which desolvation is performed so that the dry polymer may be obtained. The deprotecting step can be performed simultaneously with the desolvating step by, for example, steam stripping.

In the present invention, the target modified conjugated diene-based polymer can be obtained by performing the following deprotecting step. A group derived from a silicon atom compound bonded to the active end of the conjugated diene-based polymer is subjected to a hydrolysis treatment so that the protected primary amino group in the group may be converted into an amino group as a free radical.

In the hydrolyzing step in the production method of the present invention to be preferably provided between the modifying step and the deprotecting step, or after the deprotecting step or simultaneously with the deprotecting step, a hydrolysis reaction is performed after the completion of the modifying step in the presence of water under an acidic, neutral, or alkaline condition. Thus, the hydrolyzable functional group bonded to the modified conjugated diene-based polymer is efficiently hydrolyzed so that a silanol group may be produced at an end or side chain of the modified conjugated diene-based polymer.

The amount of water to be used in the hydrolysis reaction is preferably a molar amount in excess of the molar amount of Li of the initiator, for example, such as a molar amount two to four times as large as the molar amount of Li of the initiator. A hydrolysis time is typically about ten minutes to several hours.

It should be noted that when the hydrolysis reaction is performed under an alkaline condition, an alkali metal hydroxide such as sodium hydroxide or potassium hydroxide, preferably sodium hydroxide is desirably added as a basic compound, and when the hydrolysis reaction is performed under an acidic condition, an inorganic acid such as hydrochloric acid, sulfuric acid, or nitric acid, a carboxylic acid such as acetic acid or formic acid, silicon tetrachloride, or the like is desirably added as an acidic compound.

In the foregoing, that the hydrolyzing step is performed simultaneously with the deprotecting step means that the deprotecting step and the hydrolyzing step are performed in a single step.

In the present invention, a condensation reaction step of performing a condensation reaction in the presence of a condensation-accelerating agent can be further provided between the modifying step and the deprotecting step or the hydrolyzing step.

The condensation-accelerating agent to be used in the condensation reaction is preferably added after the modification reaction and before the initiation of the condensation reaction. When the condensation-accelerating agent is added before the modification reaction, its direct reaction with an active site occurs and hence a hydrocarbyloxy group is not introduced into the active site in some cases. In addition, when the condensation-accelerating agent is added after the initiation of the condensation reaction, the condensation-accelerating agent is not uniformly dispersed and hence its catalytic performance reduces in some cases.

When the condensation reaction step is provided between the modifying step and the hydrolyzing step, the timing at which the condensation-accelerating agent is added is typically 5 minutes to 5 hours after the initiation of the modification reaction, preferably 15 minutes to 1 hour after the initiation of the modification reaction. When the condensation reaction step is provided after the hydrolyzing step, the timing is typically 5 minutes to 5 hours after the initiation of the hydrolysis reaction, preferably 10 minutes to 2 hours after the initiation.

The condensation-accelerating agent is preferably a compound containing a metal element, and is more preferably a compound containing at least one kind of metal belonging to any one of Groups 2 to 15 of the periodic table.

The condensation-accelerating agent containing a metal element is suitably as described below. The agent contains at least one kind selected from Ti, Sn, Bi, Zr and Al, and is an alkoxide, carboxylate, or acetylacetonate complex salt of the metal.

An alkoxide, carboxylate, and acetylacetonate complex salt of titanium (Ti) are each preferably used as a condensation-accelerating agent containing Ti as a metal component.

Specific examples thereof include tetrakis(2-ethyl-1,3-hexanediolato)titanium, tetrakis(2-methyl-1,3-hexanediolato)titanium, tetrakis(2-propyl-1,3-hexanediolato)titanium, tetrakis(2-butyl-1,3-hexanediolato)titanium, tetrakis(1,3-hexanediolato)titanium, tetrakis(1,3-pentanediolato)titanium, tetrakis(2-methyl-1,3-pentanediolato)titanium, tetrakis(2-ethyl-1,3-pentanediolato)titanium, tetrakis(2-propyl-1,3-pentanediolato)titanium, tetrakis(2-butyl-1,3-pentanediolato)titanium, tetrakis(1,3-heptanediolato)titanium, tetrakis(2-methyl-1,3-heptanediolato)titanium, tetrakis(2-ethyl-1,3-heptanediolato)titanium, tetrakis(2-propyl-1,3-heptanediolato)titanium, tetrakis(2-butyl-1,3-heptanediolato)titanium, tetrakis(2-ethylhexoxy)titanium, tetramethoxytitanium, tetraethoxytitanium, tetra-n-propoxytitanium, tetraisopropoxytitanium, tetra-n-butoxytitanium, a tetra-n-butoxytitanium oligomer, tetraisobutoxytitanium, tetra-sec-butoxytitanium, tetra-tert-butoxytitanium, bis(oleato)bis(2-ethylhexanoato)titanium, titanium dipropoxybis(triethanolaminate), titanium dibutoxybis(triethanolaminate), titanium tributoxystearate, titanium tripropoxystearate, titanium tripropoxyacetylacetonate, titanium dipropoxybis(acetylacetonate), titanium tripropoxy(ethylacetoacetate), titanium propoxyacetylacetonatobis(ethylacetoacetate), titanium tributoxyacetylacetonate, titanium dibutoxybis(acetylacetonate), titanium tributoxyethylacetoacetate, titanium butoxyacetylacetonatobis(ethylacetoacetate), titanium tetrakis(acetylacetonate), titanium diacetylacetonatobis(ethylacetoacetate), bis(2-ethylhexanoato)titanium oxide, bis(laurato)titanium oxide, bis(naphthenato)titanium oxide, bis(stearato)titanium oxide, bis(oleato)titanium oxide, bis(linolato)titanium oxide, tetrakis(2-ethylhexanoato)titanium, tetrakis(laurato)titanium, tetrakis(naphthenato)titanium, tetrakis(stearato)titanium, tetrakis(oleato)titanium, tetrakis(linolato)titanium, titanium di-n-butoxide(bis-2,4-pentanedionate), titanium oxide bis(stearate), titanium oxide bis(tetramethylheptanedionate), titanium oxide bis(pentanedionate), and titanium tetra(lactate).

Of those, tetrakis(2-ethyl-1,3-hexanediolato)titanium, tetrakis(2-ethylhexoxy)titanium, and titanium di-n-butoxide (bis-2,4-pentanedionate) are preferred.

A condensation-accelerating agent containing Sn as a metal complex is preferably a tin compound having an oxidation number of 2 represented by $Sn(OCOR^{31})_2$ (where $R^{31}$ represents an alkyl group having 2 to 19 carbon atoms) or a tin compound having an oxidation number of 4 represented by $R^{32}_x SnA^5_y B^1_{4-y-x}$ (where $R^{32}$ represents an aliphatic hydrocarbon group having 1 to 30 carbon atoms, x represents an integer of 1 to 3, y represents 1 or 2, $A^5$ represents a group selected from a carboxyl group having 2 to 30 carbon atoms, a β-dicarbonyl group having 5 to 20 carbon atoms, a hydrocarbyloxy group having 3 to 20 carbon atoms, and a siloxy group trisubstituted with a hydrocarbyl group having 1 to 20 carbon atoms and/or a hydrocarbyloxy group having 1 to 20 carbon atoms, and $B^1$ represents a hydroxyl group or a halogen atom).

More specifically, a dicarboxylate of divalent tin, a dicarboxylate (comprehending a bis(hydrocarbyldicarboxylate)), bis(β-diketonate), alkoxy halide, monocarboxylic acid salt hydroxide, alkoxy(trihydrocarbylsiloxide), alkoxy(dihydrocarbylalkoxysiloxide), bis(trihydrocarbylsiloxide), or bis(dihydrocarbylalkoxysiloxide) of tetravalent dihydrocarbyltin, or the like can be suitably used as the carboxylate of tin. A hydrocarbyl group bonded to tin is desirably a group having 4 or more carbon atoms, and is particularly preferably a group having 4 to 8 carbon atoms.

In addition, a condensation-accelerating agent containing Zr, Bi, or Al as a metal component (such as an alkoxide, carboxylate, or acetylacetonate complex salt of any such metal) is, for example, any one of the following compounds (a) to (e).
 (a) carboxylic acid salt of bismuth
 (b) alkoxide of zirconium
 (c) carboxylic acid salt of zirconium
 (d) alkoxide of aluminum
 (e) carboxylic acid salt of aluminum Specific examples thereof include: tris(2-ethylhexanoato)bismuth, tris(laurato)bismuth, tris(naphthenato)bismuth, tris(stearato)bismuth, tris(oleato)bismuth, and tris(linolato)bismuth;

tetraethoxyzirconium, tetra-n-propoxyzirconium, tetraisopropoxyzirconium, tetra-n-butoxyzirconium, tetra-sec-butoxyzirconium, tetra-tert-butoxyzirconium, tetra(2-ethylhexoxy)zirconium, zirconium tributoxystearate, zirconium tributoxyacetylacetonate, zirconium butoxybis(acetylacetonate), zirconium tributoxyethylacetoacetate, zirconium butoxyacetylacetonatobis(ethylacetoacetate), zirconium tetrakis(acetylacetonate), zirconium diacetylacetonatobis(ethylacetoacetate), bis(2-ethylhexanoato)zirconium oxide, bis(laurato)zirconium oxide, bis(naphthenato)zirconium oxide, bis(stearato)zirconium oxide, bis(oleato)zirconium oxide, bis(linolato)zirconium oxide, tetrakis(2-ethylhexanoato)zirconium, tetrakis(laurato)zirconium, tetrakis(naphthenato)zirconium, tetrakis(stearato)zirconium, tetrakis(oleato)zirconium, and tetrakis(linolato)zirconium; and triethoxyaluminum, tri-n-propoxyaluminum, triisopropoxyaluminum, tri-n-butoxyaluminum, tri-sec-butoxyaluminum, tri-tert-butoxyaluminum, tri(2-ethylhexoxy)aluminum, aluminum dibutoxystearate, aluminum dibutoxyacetylacetonate, aluminum butoxybis(acetylacetonate), aluminum dibutoxyethylacetoacetate, aluminum tris(acetylacetonate), aluminum tris(ethylacetoacetate), tris(2-ethylhexanoato)aluminum, tris(laurato)aluminum, tris(naphthenato)aluminum, tris(stearato)aluminum, tris(oleato)aluminum, and tris(linolato)aluminum.

Of those, tris(2-ethylhexanoato)bismuth, tetra-n-propoxyzirconium, tetra-n-butoxyzirconium, bis(2-ethylhexanoato)zirconium oxide, bis(oleato)zirconium oxide, triisopropoxyaluminum, tri-sec-butoxyaluminum, tris(2-ethylhexanoato)aluminum, tris(stearato)aluminum, zirconium tetrakis(acetylacetonate), and aluminum tris (acetylacetonate) are preferred.

The compounding amount (usage) of the condensation-accelerating agent is preferably such an amount as to be 0.1 to 10 parts by mass based on 100 parts by mass of the rubber component in a rubber composition to be described later. The compounding amount is more preferably 0.5 to 5 parts by mass. Setting the usage of the condensation-accelerating agent within the range allows the condensation reaction to progress efficiently.

The condensation reaction is preferably carried out in an aqueous solution, and the temperature during the condensation reaction is preferably 85 to 180° C., more preferably 100 to 170° C., particularly preferably 110 to 150° C. Through controlling the temperature during the condensation reaction to fall within the range, the condensation reaction can be efficiently completed, whereby deterioration in quality and the like of the produced modified conjugated diene-based polymer because of time-dependent aging reaction of the polymer and the like can be prevented.

It should be noted that the condensation reaction time is preferably about 5 minutes to 10 hours, more preferably about 15 minutes to 5 hours. Through controlling the condensation reaction time to fall within the range, the condensation reaction can be smoothly completed.

The pressure of the reaction system during the condensation reaction is preferably 0.01 to 20 MPa, more preferably 0.05 to 10 MPa.

No particular limitation is imposed on the mode with which the condensation reaction is performed, and a batch-type reactor may be employed. Alternatively, the reaction may be carried out in a continuous manner by means of an apparatus such as a multi-step continuous reactor. In the course of the condensation reaction, desolvation may be simultaneously performed.

After the completion of the deprotecting step or of the deprotecting step and the condensation reaction step, for example, a solution of 2,6-di-t-butyl-p-cresol (BHT) in isopropanol is added to a polymerization reaction system to terminate the polymerization reaction.

After that, a desolvation treatment such as steam stripping involving blowing in steam to reduce the partial pressure of the solvent or a vacuum drying treatment is performed. Thus, the modified conjugated diene-based polymer of the present invention is obtained.

Here, when the hydrocarbyloxysilane compound having a protected primary amino group is used in the modifying step, a deprotection treatment in which the protective group of a protected nitrogen atom is caused to leave so that a primary amino group may be produced is simultaneously performed in a desolvation treatment step involving using steam such as steam stripping described above. In addition to the foregoing, the deprotection treatment of the protected primary amino group derived from the hydrocarbyloxysilane compound can be performed by hydrolyzing the protective group on the primary amino group according to any one of the various methods to convert the group into a free primary amino group as required at any one of the stages ranging from a stage after the completion of the modifying step to the stage at which desolvation is performed so that a dry polymer may be obtained.

Next, the modified conjugated diene-based polymer obtained by the production method of the present invention is described.

The modified conjugated diene-based polymer of the present invention preferably has, at a molecular end of the conjugated diene-based polymer, a silanol group and a functional group in the vicinity of the silanol group, the functional group accelerating a reaction between the silanol group and a reinforcing filler.

The modified conjugated diene-based polymer of the present invention is preferably such that only one silanol group exists in its molecular chain. This is because of the following reason. When two or more silanol groups exist in the molecular chain, the silanol groups condense each other. As a result, the viscosity of the modified conjugated diene-based polymer increases, thereby making it difficult to perform its kneading operation in some cases.

In addition, the modified conjugated diene-based polymer of the present invention has both the silanol group, and the functional group in the vicinity of the silanol group for accelerating the reaction between the silanol group and the reinforcing filler. Accordingly, low heat generating property is improved in each of a silica-compounded rubber composition and a carbon black-compounded rubber composition as compared with: a modified conjugated diene-based polymer having only a silanol group, and free of any functional group for accelerating a reaction between the silanol group and the reinforcing filler; and a modified conjugated diene-based polymer having only a functional group for accelerating a reaction between a silanol group and the reinforcing filler, and free of any silanol group.

In the present invention, a primary amino group or a protected primary amino group is effective as a group for accelerating a reaction with the filler.

The vinyl bond content of the conjugated diene portion of the modified conjugated diene-based polymer of the present invention, which is not limited, is preferably 70% or less. A vinyl bond content of 70% or less is preferred because a fracture characteristic and an abrasion characteristic are improved when the polymer is used in a tire tread.

In addition, the polymer preferably has a styrene content of 0 to 50 mass %. This is because a styrene content of 50 mass % or less improves a balance between its low heat generating property and wet skid performance.

It should be noted that the vinyl bond content was determined by an infrared method (Morero method) and the styrene content was determined by calculating the integration ratio of a $^1$H-NMR spectrum.

A rubber composition of the present invention contains the modified conjugated diene-based polymer of the present invention, and preferably further contains a condensation-accelerating agent.

The modified conjugated diene-based polymer to be incorporated as an essential component into the rubber composition of the present invention may be a modified conjugated diene-based polymer obtained by the production method of the present invention, the polymer being obtained by performing a modification reaction, a deprotection reaction, and in some cases, a condensation reaction involving using a condensation-accelerating agent, or may be a modified conjugated diene-based polymer obtained without through the condensation reaction involving using a condensation-accelerating agent.

The rubber composition of the present invention can further contain a condensation-accelerating agent.

The condensation-accelerating agent may be added at the time of the synthesis of the modified conjugated diene-based polymer like the production method of the present invention, or may be added at the time of the preparation of the rubber composition. Alternatively, those operations may be combined.

Information about the condensation-accelerating agent is as described in the condensation reaction in the method of producing a modified conjugated diene-based polymer.

When the condensation-accelerating agent is added at the time of the preparation of the rubber composition, the agent is preferably kneaded with any other component at a first stage at a temperature of typically about 20 to 185° C., more preferably 60 to 175° C.

The content of the condensation-accelerating agent in the rubber composition is preferably 0.1 to 10 parts by mass based on 100 parts by mass of the rubber component from the viewpoint of reactivity between silica and silanol, and is more preferably 0.5 to 5 parts by mass.

The rubber component of the rubber composition of the present invention is preferably formed of 10 to 100 mass % of the modified conjugated diene-based polymer and 90 to 0 mass % of a diene-based rubber. This is because when the content of the modified conjugated diene-based polymer is 10 mass % or more, the effect of the present invention can be enjoyed. Here, examples of the diene-based rubber include a polybutadiene, a polyisoprene, a polybutadiene-polyisoprene copolymer, a styrene-butadiene copolymer, a styrene-isoprene copolymer, a styrene-isoprene-butadiene terpolymer, an ethylene-propylene-diene terpolymer, a butyl rubber, and a halogenated butyl rubber except the modified conjugated diene-based polymer according to the present invention.

The rubber composition of the present invention contains preferably 10 to 200 parts by mass, more preferably 20 to 120 parts by mass, particularly preferably 30 to 100 parts by mass of a reinforcing filler based on 100 parts by mass of the rubber component formed of 10 to 100 mass % of the modified conjugated diene-based polymer of the present invention and 90 to 0 mass % of a diene-based rubber. In addition, the reinforcing filler is preferably carbon black and/or silica. The reinforcing filler is particularly preferably silica.

Carbon black to be used as the reinforcing filler is not particularly limited, and for example, a GPF, FEF, SRF, HAF, N339, IISAF, ISAF, or SAF is used. Carbon black having a nitrogen adsorption specific surface area ($N_2SA$, measured in conformity with JIS K 6217-2:2001) of 20 to 250 $m^2/g$ is preferred.

Any one of the various commercial products can be used as silica to be used as the reinforcing filler in combination with carbon black as desired or alone. Of those, wet silica, dry silica, or colloidal silica is preferably used, and wet silica is particularly preferably used. The BET specific surface area (measured in conformity with ISO 5794/1) of silica is preferably 100 $m^2/g$ or more, more preferably 150 $m^2/g$ or more, particularly preferably 170 $m^2/g$ or more. A commercial product such as a product available under the trade name "Nipsil AQ" (BET specific surface area=190 $m^2/g$) or "Nipsil KQ" from TOSOH SILICA CORPORATION, or a product available under the trade name "Ultrasil VN3" (BET specific surface area=175 $m^2/g$) from Degussa can be used as such silica.

When silica is used as a filler in the rubber composition of the present invention, a silane coupling agent can be compounded thereinto for the purpose of further improving the reinforcing property and the low heat generating property.

The silane coupling agent includes, for example, bis(3-triethoxysilylpropyl)tetrasulfide, bis(3-triethoxysilylpropyl)trisulfide, bis(3-triethoxysilylpropyl)disulfide, bis(2-triethoxysilylethyl)tetrasulfide, bis(3-trimethoxysilylpropyl)tetrasulfide, bis(2-trimethoxysilylethyl)tetrasulfide, 3-mercaptopropyltrimethoxysilane, 3-mercaptopropyltriethoxysilane, 2-mercaptoethyltrimethoxysilane, 2-mercaptoethyltriethoxysilane, 3-trimethoxysilylpropyl-N, N-dimethylthiocarbamoyl tetrasulfide, 3-triethoxysilylpropyl-N,N-dimethylthiocarbamoyl tetrasulfide, 2-triethoxysilylethyl-N, N-dimethylthiocarbamonyl tetrasulfide, 3-trimethoxysilylpropylbenzothiazolyl tetrasulfide, 3-triethoxysilylpropylbenzolyl tetrasulfide, 3-triethoxysilylpropylmethacrylate monosulfide, 3-trimethoxysilylpropylmethacrylate monosulfide, bis(3-diethoxymethylsilylpropyl) tetrasulfide, 3-mercaptopropyldimethoxymethylsilane, dimethoxymethylsilylpropyl-N,N-dimethylthiocarbamoyl tetrasulfide, and dimethoxymethylsilylpropylbenzothiazolyl tetrasulfide. Of those, bis(3-triethoxysilylpropyl)polysulfide and 3-trimethoxysilylpropylbenzothiazyl tetrasulfide are suited in terms of an effect of improving the reinforcing property and the like.

Those silane coupling agents may be used alone or in combination of two or more kinds thereof.

The rubber composition of the present invention employs, as a rubber component, a modified polymer in which a functional group having a high affinity to silica is introduced into an active site of the molecule thereof. Therefore, the compounding amount of the silane coupling agent can be reduced as compared to the general cases. The compounding amount of the silane coupling agent, which varies depending on the kind of the agent, preferably falls within the range of 1 to 20 mass % based on silica. When the amount falls within the range, gelation of the rubber component may be prevented while attaining the effect of the coupling agent sufficiently. From the viewpoints of the effect of coupling agent and prevention of gelation, the compounding amount of the silane coupling agent preferably falls within the range of 5 to 15 mass %.

The rubber composition according to the present invention is preferably sulfur-crosslinkable and sulfur is suitably used as a vulcanizing agent. With regard to its usage, a sulfur content (total amount of sulfur and the sulfur content of a sulfur-donating agent) is preferably compounded in an amount of 0.1 to 10 parts by mass based on 100 parts by mass of the rubber component. This is because when the usage falls within the range, an elastic modulus and strength required of a vulcanized rubber composition are secured, and low fuel consumption can be obtained. From the viewpoint, the sulfur content is more preferably compounded in an amount of 0.2 to 8 parts by mass.

Any one of the various chemicals to be typically used in the rubber industry such as a vulcanizing agent except sulfur, a vulcanization-accelerating agent, a process oil, a plasticizer, an antioxidant, a scorch preventive, zinc white, stearic acid, a thermosetting resin, and a thermoplastic resin can be incorporated into the rubber composition according to the present invention as desired to such an extent that the object of the present invention is not impaired.

The vulcanization-accelerating agent which can be used in the present invention is not specifically limited, and may include thiazole-based vulcanization-accelerating agents such as 2-mercaptobenzothiazole (M), dibenzothiazyl disulfide (DM), and N-cyclohexyl-2-benzothiazylsulfenamide (CZ), and guanidine-based vulcanization-accelerating agents such as diphenylguanidine (DPG). The usage thereof is preferably 0.1 to 5.0 parts by mass, more preferably 0.2 to 3.0 parts by mass based on 100 parts by mass of the rubber component.

In addition, the process oil which can be used as a softening agent in the rubber composition of the present invention includes a paraffin-based oil, a naphthene-based oil, and an aromatic-based oil. The aromatic-based oil is used for uses in which the tensile strength and the abrasion resistance are regarded as important, and the naphthene-based oil or the paraffin-based oil is used for uses in which the hysteresis loss and the low-temperature characteristic are regarded as important. The usage thereof is preferably 0 to 100 parts by mass based on 100 parts by mass of the rubber component, and when the amount is 100 parts by mass or less, deterioration in the tensile strength and the low heat generating property (low fuel consumption) of the vulcanized rubber is suppressed.

Further, an antioxidant that can be used in the rubber composition of the present invention is, for example, 3C(N-isopropyl-N'-phenyl-p-phenylenediamine), 6C[N-(1,3-dimethylbutyl)-N'-phenyl-p-phenylenediamine], AW(6-ethoxy-2,2,4-trimethyl-1,2-dihydroquinoline), or a high-temperature condensation product of diphenylamine and acetone. The usage of the antioxidant is preferably 0.1 to 6.0 parts by mass, more preferably 0.3 to 5.0 parts by mass based on 100 parts by mass of the rubber component.

The rubber composition of the present invention is obtained by kneading according to the compounding formulation with a kneading machine such as a Banbury mixer, a roll, or an internal mixer. The composition is subjected to molding, and is then vulcanized. As a result, a rubber composition excellent in low heat generating property and abrasion resistance can be obtained. The rubber composition is used in various members of pneumatic tires and various industrial rubber products such as a belt conveyor and a rubber hose.

EXAMPLES

Hereinafter, the present invention is described in further details with reference to examples. However, the present invention is by no means limited to these examples.

It should be noted that the dynamic loss tangent (tan δ) and abrasion resistance of the vulcanized rubber composition of a modified conjugated diene-based polymer were measured in accordance with the following methods. In addition, the condensation degree (m) of a modifying agent was measured by the following method.

<Condensation Degree of Modifying Agent>
(1) Condensation Degree (m) of Modifying Agent The condensation degree was calculated from integration values for both the peak value of an end portion and a peak value derived from a protective group in each of GPC and NMR.

<Silanol Production Ratio of Modified Conjugated Diene-Based Polymer>
(1) Silanol Production Ratio The hydrolysis amount of an alkoxysilane group is described in the example of an ethoxysilyl group. An alkoxysilane amount M (%) of the modified polymer was calculated from a multiband around 3.6 to 3.7 ppm characteristic of $SiOCH_2CH_3$ of the polymer in 1H-NMR and the number-average molecular weight of a base portion. A ratio $R_{GPC}$ % of an uncoupled component in GPC was calculated from the peak area of a base-equivalent component based on the amount of an injected sample in GPC. In order that a post-reaction component of coupling or the like might be subtracted, a difference between the M (%) and the $R_{GPC}$ % was determined, and then a silanol production number was calculated from the difference in terms of percentage. A number-average molecular weight determined from GPC corrected with Mark-Houwink's equation was applied to the number-average molecular weight to be used in the calculation of the silanol production ratio.

<Physical Properties of Vulcanized Rubber>
(1) Dynamic Loss Tangent (Tan δ)

A tan δ was measured with a viscoelasticity-measuring apparatus (manufactured by Rheometrics, Inc.) at a temperature of 60° C., a strain of 5%, and a frequency of 15 Hz. Shown in Table 1 was an index determined from the following equation with the tan δ of Comparative Example 1 set to 100. A smaller index value means that low heat generating property is better and hysteresis loss is smaller. Dynamic loss tangent (tan δ) index={(tan δ of vulcanized rubber composition under test)/(tan δ of vulcanized rubber composition of Comparative Example 1, 2, or 5)}×100

(2) Abrasion Resistance (Lambourn)

The result of a JIS K 6264-1993 Lambourn abrasion test was represented as an index calculated from the following equation with the result of Comparative Example 1 or 3 set to 100.

Abrasion resistance index=(abrasion loss of Comparative Example 1,2, or 5/abrasion loss of sample under test)×100

A larger abrasion resistance index means that abrasion resistance is more excellent.

Synthesis of Modifying Agent

Synthesis Example 1

Synthesis of N,N-bis(trimethylsilyl)aminopropyltriethoxysilane

Under a nitrogen atmosphere, 41 g of 3-aminopropyltriethoxysilane (manufactured by Gelest, Inc.) for forming an aminosilane moiety were added to 400 ml of a dichloromethane solvent in a glass flask equipped with a stirring machine. Subsequently, 48 ml of trimethylsilane chloride (manufactured by Sigma-Aldrich, Inc) and 53 ml of triethylamine for forming a protective moiety were added to the solution, followed by stirring the mixture at room temperature for 17 hours. The reaction solution was then subjected to an evaporator so that the solvent was removed. Thus, a composition reaction solution was obtained. Further, the resultant reaction solution was distilled under reduced pressure under the condition of 5 mm/Hg. Thus, 40 g of N,N-bis(trimethylsilyl)aminopropyltriethoxysilane were obtained as a fraction at 125 to 130° C.

Synthesis Example 2

Synthesis of Complete Condensation Product of N,N-bis(trimethylsilyl)aminopropyltriethoxysilane Under a nitrogen atmosphere, 41 g of 3-aminopropyltriethoxysilane (manufactured by Gelest, Inc.) for forming an aminosilane moiety were added to 400 ml of a dichloromethane solvent in a glass flask equipped with a stirring machine. Subsequently, 48 ml of trimethylsilane chloride (manufactured by Sigma-Aldrich, Inc) and 53 ml of triethylamine for forming a protective moiety were added to the solution, followed by stirring the mixture at room temperature for 25 hours. The reaction solution was then subjected to an evaporator so that the solvent was removed. Thus, a composition reaction solution was obtained. Further, the resultant reaction solution was distilled under reduced pressure under the condition of 5 mm/Hg. Thus, a complete condensation product of N,N-bis(trimethylsilyl)aminopropyltriethoxysilane was obtained as a fraction at 150 to 200° C. The condensation degree m was 4.1.

Synthesis Example 3

Synthesis of Complete Condensation Product of N,N-bis(trimethylsilyl)aminopropyltriethoxysilane Under a nitrogen atmosphere, 41 g of 3-aminopropyltriethoxysilane (manufactured by Gelest, Inc.) for forming an aminosilane moiety were added to 400 ml of a dichloromethane solvent in a glass flask equipped with a stirring machine. Subsequently, 48 ml of trimethylsilane chloride (manufactured by Sigma-Aldrich, Inc) and 53 ml of triethylamine for forming a protective moiety were added to the solution, followed by stirring the mixture at 50° C. for 48 hours. The reaction solution was then subjected to an evaporator so that the solvent was removed. Thus, a composition reaction solution was obtained. Further, the resultant reaction solution was distilled under reduced pressure under the condition of 5 mm/Hg. Thus, a complete condensation product of N,N-bis(trimethylsilyl)aminopropyltriethoxysilane was obtained as a fraction at 150 to 200° C. The condensation degree m was 4.1.

Synthesis Example 4

Synthesis of complete condensation Product of N,N-bis(trimethylsilyl)aminopropyltriethoxysilane and N,N-bis(dimethyl)aminopropyltriethoxysilane Under a nitrogen atmosphere, 20 g of N,N-bis(trimethylsilyl)aminopropyltriethoxysilane obtained in Synthesis Example 1 were added to 400 ml of a dichloromethane solvent in a glass flask provided with a stirring machine. After that, a dichloromethane solution in which 20 g of N,N-bis(dimethyl)aminopropyltriethoxysilane had been dissolved was dropped while the contents in the flask were stirred under room temperature. After that, the mixture was stirred for 25 hours under room temperature, and then the reaction solution was subjected to an evaporator so that the solvent was removed. Thus, a composition reaction solution was obtained. Further, the resultant reaction solution was distilled under reduced pressure under the condition of 5 mm/Hg. Thus, a complete condensation product of N,N-bis(trimethylsilyl)aminopropyltriethoxysilane and N,N-bis(dimethyl)aminopropyltriethoxysilane was obtained as a fraction at 150 to 200° C.

Synthesis Example 5

Synthesis of Ketimine Silane Condensation Product

Under a nitrogen atmosphere, 20.0 g (0.112 mol) of 3-aminopropyltrimethoxysilane and 10.7 g (0.123 mol) of methyl isopropyl ketone were stirred at room temperature for 2 days. Methanol and unreacted methyl isopropyl ketone were removed from the resultant reaction solution under vacuum. Thus, a ketimine silane condensation product having an average condensation degree of 2.4 was obtained.

Production Example 1

Production of Modified Conjugated Diene Copolymer A

<Production of Conjugated Diene Copolymer Having Active Site>

A solution of 1,3-butadiene in cyclohexane and a solution of styrene in cyclohexane were added to an 800-mL pressure-resistant glass vessel that had been dried and replaced with nitrogen so that the amount of 1,3-butadiene was 60 g and the amount of styrene was 15 g. 0.70 Millimole of 2,2-ditetrahydrofurylpropane was added to the mixture. Further, 0.70 mmol of n-butyllithium (BuLi) was added to the mixture, and then the mixture was subjected to a polymerization reaction in a hot water bath at 50° C. for 1.5 hours. A polymerization conversion degree at that time was nearly 100%.
<Modifying Step>
Next, the complete condensation product of the organosilane compound obtained in Synthesis Example 2 was added to the polymerization reaction system in an equimolar amount based on lithium (Li). Further, a modification reaction was performed at 50° C. for 30 minutes.
<Hydrolyzing Step and any Subsequent Step>
After that, 1.5 ml of dilute hydrochloric acid were gradually added to the polymerization reaction system. Next, water was added to the polymerization reaction system in a molar amount three times as large as that of lithium (Li), and then the polymerization reaction system was stirred for 30 minutes. Next, a solution of 2,6-di-tert-butyl-p-cresol in isopropanol was added to the polymerization reaction system to terminate the polymerization reaction. After that, desolvation was performed by blowing steam into the system to reduce the partial pressure of the solvent (steam stripping). After that, vacuum drying was performed. Thus, a modified conjugated diene copolymer A was obtained.

Production Example 2

Production of Modified Conjugated Diene Copolymer B

<Production of Conjugated Diene Copolymer Having Active Site>

A solution of 1,3-butadiene in cyclohexane and a solution of styrene in cyclohexane were added to an 800-mL pressure-resistant glass vessel that had been dried and replaced with nitrogen so that the amount of 1,3-butadiene was 60 g and the amount of styrene was 15 g. 0.70 Millimole of 2,2-ditetrahydrofurylpropane was added to the mixture. Further, 0.70 mmol of n-butyllithium (BuLi) was added to the mixture, and then the mixture was subjected to a polymerization reaction in a hot water bath at 50° C. for 1.5 hours. A polymerization conversion degree at that time was nearly 100%.
<Modifying Step>
Next, the complete condensation product of the organosilane compound obtained in Synthesis Example 3 was added to the polymerization reaction system in an equimolar amount based on lithium (Li). Further, a modification reaction was performed at 50° C. for 30 minutes.
<Any Subsequent Step>
After that, a solution of 2,6-di-tert-butyl-p-cresol in isopropanol was added to the polymerization reaction system to terminate the polymerization reaction. After that, deprotection and desolvation were performed by blowing steam into the system to reduce the partial pressure of the solvent (steam stripping). After that, vacuum drying was performed. Thus, a modified conjugated diene copolymer B was obtained.

Production Example 3

Production of Modified Conjugated Diene Copolymer C

A modified conjugated diene copolymer C was obtained in the same manner as in Production Example 1 except that no hydrolyzing step was provided.

Production Example 4

Production of Modified Conjugated Diene Copolymer D

A modified conjugated diene copolymer D was obtained in the same manner as in Production Example 1 except that: the complete condensation product of N,N-bis(trimethylsilyl)aminopropyltriethoxysilane and N,N-bis(dimethyl)aminopropyltriethoxysilane obtained in Synthesis Example 4 was added as a modifying agent in the modifying step instead of the complete condensation product of N,N-bis(trimethylsilyl)aminopropyltriethoxysilane obtained in Synthesis Example 2; and no hydrolyzing step was provided.

Production Comparative Example 1

Production of Modified Conjugated Diene Copolymer E

A modified conjugated diene copolymer E was obtained in the same manner as in Production Example 1 except that the uncondensed N,N-bis(trimethylsilyl)aminopropyltriethoxysilane obtained in Synthesis Example 1 was added as a modifying agent in the modifying step instead of the complete condensation product of N,N-bis(trimethylsilyl)aminopropyltriethoxysilane obtained in Synthesis Example 2.

Production Comparative Example 2

Production of Modified Conjugated Diene Copolymer F

A modified conjugated diene copolymer F was obtained in the same manner as in Production Example 2 except that the uncondensed N,N-bis(trimethylsilyl)aminopropyltriethoxysilane obtained in Synthesis Example 1 was added as a modifying agent in the modifying step instead of the complete condensation product of N,N-bis(trimethylsilyl)aminopropyltriethoxysilane obtained in Synthesis Example 3.

Production Comparative Example 3

Production of Modified Conjugated Diene Copolymer G

A modified conjugated diene copolymer G was obtained in the same manner as in Production Example 1 except that: the uncondensed N,N-bis(trimethylsilyl)aminopropyltriethoxysilane obtained in Synthesis Example 1 was added as a modifying agent in the modifying step instead of the complete condensation product of N,N-bis(trimethylsilyl)aminopropyltriethoxysilane obtained in Synthesis Example 2; and no hydrolyzing step was provided.

Production Comparative Example 4

Production of Modified Conjugated Diene Copolymer H

A modified conjugated diene copolymer H was obtained in the same manner as in Production Example 1 except that: the ketimine silane condensation product obtained in Synthesis Example was added as a modifying agent in the modifying step instead of the complete condensation product of N,N-bis(trimethylsilyl)aminopropyltriethoxysilane obtained in Synthesis Example 2; and no hydrolyzing step was provided.

Example 1 and Comparative Example 1

The silanol production ratios of the modified conjugated diene copolymers A and E obtained in Production Example 1 and Production Comparative Example 1 were measured. In addition, two kinds of rubber compositions of Example 1 and Comparative Example 1 were each prepared in accordance with the formulation of "Composition 1" shown in Table 1. Table 2 shows the results of the abrasion resistance and tan $\delta$ of each of the rubber compositions after their vulcanization.

Examples 2 to 4 and Comparative Examples 2 to 4

The silanol production ratios of the modified conjugated diene copolymers A, C, D, E, G, and H obtained in Production Examples 1, 3, and 4 and Production Comparative Examples 1, 3, and 4 were measured. In addition, six kinds of rubber compositions of Examples 2 to 4 and Comparative Examples 2 to 4 were each prepared in accordance with the formulation of "Composition 2" shown in Table 1. Table 3 shows the results of the abrasion resistance and tan $\delta$ of each of the rubber compositions after their vulcanization.

Example 5 and Comparative Example 5

The condensation degrees of the modified conjugated diene copolymers B and E obtained in Production Example 2 and Production Comparative Example 2 were measured. In addition, two kinds of rubber compositions of Example 2 and Comparative Example 3 were each prepared in accordance with the compounding formulation shown in Table 1. Table 4 shows the results of the abrasion resistance and tan $\delta$ of each of the rubber compositions after their vulcanization.

TABLE 1

| Kneading stage | Compounding formulation (part(s) by mass) | Composition 1 | Composition 2 |
|---|---|---|---|
| First Stage | Modified conjugated diene-based polymer*[1] | 50 | 80 |
| | Polyisoprene rubber*[2] | 50 | 20 |
| | Aroma oil*[3] | 10 | 10 |
| | Carbon black (ISAF-HS)*[4] | 25 | 30 |
| | Silica*[5] | 27.5 | 25 |
| | Silane coupling agent*[6] | 2.75 | 2.5 |
| | Stearic acid | 2 | 2 |
| | Antioxidant 6C*[7] | 1 | 1 |
| Second Stage | Zinc white | 3 | 3 |
| | Vulcanization-accelerating agent DPG*[8] | 0.75 | 0.75 |
| | Vulcanization-accelerating agent DM*[9] | 0.75 | 0.75 |
| | Vulcanization-accelerating agent NS*[10] | 0.75 | 0.75 |
| | Sulfur | 1.5 | 1.5 |

[Notes]
*[1]Modified conjugated diene-based polymer: the modified conjugated diene copolymers A to H obtained in Production Examples 1 to 4 and Production Comparative Examples 1 to 4
*[2]Polyisoprene rubber: a product available under the trade name "IR2200" from JSR Corporation
*[3]Aromatic oil: a product available under the trademark "AROMAX #3" from Fuji Kosan Co., Ltd.
*[4]Carbon black: ISAF-HS
*[5]Silica: a product available under the trademark "Nipsil AQ" from TOSOH SILICA CORPORATION
*[6]Silane coupling agent: bis(3-triethoxysilylpropyl)tetrasulfide available under the trademark "Si69" from Degussa
*[7]Antioxidant 6C: N-(1,3-dimethylbutyl)-N'-phenyl-p-phenylenediamine available under the trademark "OZONONE 6C" from Seiko Chemical Co., Ltd.
*[8]Vulcanization-accelerating agent DPG: diphenylguanidine available under the trademark "Nocceler D" from Ouchi Shinko Chemical Industrial Co., Ltd.
*[9]Vulcanization-accelerating agent DM: dibenzothiazyl disulfide available under the trademark "Nocceler DM" from Ouchi Shinko Chemical Industrial Co., Ltd.
*[10]Vulcanization-accelerating agent NS: N-t-butyl-2-benzothiazylsulfenamide available under the trademark "Nocceler NS" from Ouchi Shinko Chemical Industrial Co., Ltd.

TABLE 2

| Composition 1 | Comparative Example 1 | Example 1 |
|---|---|---|
| Presence or absence of condensation | Uncondensed | Condensed |

TABLE 2-continued

| Composition 1 | Comparative Example 1 | Example 1 |
|---|---|---|
| Conjugated diene-based polymer*1 | E | A |
| Hydrolysis | Present | Present |
| Silanol production ratio/% | 50 | 70 |
| Physical properties of vulcanized rubber (compounded with half silica) | | |
| tanδ (50° C.) (index) | 100 | 88 |
| Abrasion resistance (index) | 100 | 109 |

TABLE 3

| Composition 2 | Comparative Example 2 | Comparative Example 3 | Comparative Example 4 | Example 2 | Example 3 | Example 4 |
|---|---|---|---|---|---|---|
| Presence or absence of condensation | Uncondensed | Uncondensed | Condensed | Condensed | Condensed | Condensed |
| Conjugated diene-based polymer *1 | G | E | H | A | C | D |
| Hydrolysis | Absent | Present | Absent | Present | Absent | Absent |
| Silanol production ratio/% | 2 | 50 | 4 | 70 | 6 | 7 |
| Physical properties of vulcanized rubber (compounded with half silica) | | | | | | |
| tanδ (50° C.) (index) | 100 | 98 | 99 | 88 | 95 | 96 |
| Abrasion resistance (index) | 100 | 103 | 101 | 111 | 105 | 105 |

TABLE 4

| Composition 1 | Comparative Example 5 | Example 5 |
|---|---|---|
| Presence or absence of condensation | Uncondensed | Condensed |
| Conjugated diene-based polymer*1 | F | B |
| Hydrolysis | Absent | Absent |
| Silanol production ratio/% | 5 | 18 |
| Physical properties of vulcanized rubber (compounded with half silica) | | |
| tanδ (50° C.) (index) | 100 | 97 |
| Abrasion resistance (index) | 100 | 104 |

INDUSTRIAL APPLICABILITY

The modified conjugated diene-based polymer having low heat generating property and excellent in abrasion resistance obtained by using the modifying agent of the present invention suitably finds use in various members including: treads such as cap treads; sidewalls; and stiffeners (bead fillers); of pneumatic tires for a low heat-generating passenger car, a light car, a light truck, a truck or bus, and an off-the-road vehicle. In addition, the polymer suitably finds use in various members of various industrial rubber products such as a belt conveyor and a hose.

The invention claimed is:

1. A method of producing a modifying agent comprising a step of subjecting a silicon-containing compound having a protected primary amino group and at least two hydrolysable groups to complete condensation, wherein all monomers of the silicon-containing compound in the modifying agent are condensed such that no monomer of the silicon-containing compound remains in a resultant reaction solution obtained after the condensation, wherein the modifying agent comprises a compound represented by a general formula (1):

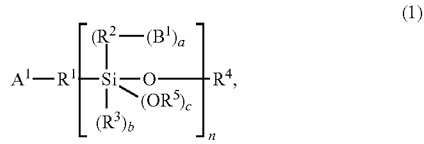

where $R^1$ and $R^2$ each represents a divalent aliphatic hydrocarbon group having 1 to 20 carbon atoms, a divalent aromatic hydrocarbon group having 6 to 18 carbon atoms, or a single bond, and may be identical to or different from each other, $R^3$, $R^4$, and $R^5$ each represents a monovalent aliphatic hydrocarbon group having 1 to 20 carbon atoms or a monovalent aromatic hydrocarbon group having 6 to 18 carbon atoms, and may be identical to or different from one another, $A^1$ represents a group for bonding the modifying agent and a conjugated diene-based polymer by adding to, or substituting for, an active site of the conjugated diene-based polymer, $B^1$ represents a primary amino group protected with a hydrolyzable protective group, a+b+c=2, a represents 1 to 2, b represents 0 to 1, and n represents 2 to 20; or a general formula (2):

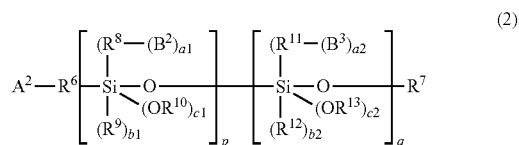

where $R^6$ and $R^{11}$ each represents a divalent aliphatic hydrocarbon group having 1 to 20 carbon atoms, a divalent aromatic hydrocarbon group having 6 to 18 carbon atoms, or a single bond, and may be identical to or different from each other, $R^8$ represents a divalent aliphatic hydrocarbon group having 1 to 20 carbon atoms or a divalent aromatic hydrocarbon group having 6 to 18 carbon atoms, $R^7$, $R^9$, $R^{10}$, $R^{12}$, and $R^{13}$ each represents a monovalent aliphatic hydrocarbon group having 1 to 20 carbon atoms or a monovalent aromatic hydrocarbon group having 6 to 18 carbon atoms, and may be identical to or different from one another, $A^2$ represents a group for bonding the modifying agent and a conjugated diene-based polymer by adding to, or substituting for, an active site of the conjugated diene-based polymer, $B^2$ represents a primary amino group protected with a hydrolyzable protective group, $B^3$ represents a linear, branched, alicyclic, or aromatic, monovalent hydrocarbon group having 1 to 30 carbon atoms and having a functional group selected from the group consisting of an isocyanate group, a thioisocyanate group, an imine residue, an amide group, a cyclic secondary amino group, an onium salt residue of a cyclic secondary amine, a non-cyclic secondary amino group, an onium salt residue of a non-cyclic secondary amine, an isocyanuric acid triester residue, a cyclic tertiary amino group, a non-cyclic tertiary amino group, a nitrile group, a pyridine residue, an onium salt residue of a cyclic tertiary amine, and an onium salt residue of a non-cyclic tertiary amine, or a linear, branched, alicyclic, or aromatic, monovalent hydrocarbon group having 1 to 30 carbon atoms which may contain at least one kind of heteroatom selected from an oxygen atom, a sulfur atom, and a phosphorus atom, a1+b1+c1=2, a1 represents 1 to 2, b1 represents 0 to 1, a2+b2+c2=2, a2, b2, and c2 each represents 0 to 2, and p and q each independently represents 1 to 10, wherein the method further comprises distilling the resultant reaction solution under reduced pressure, and obtaining a distillate fraction at 150 to 200° C.

2. The method of producing a modifying agent according to claim 1, wherein the reduced pressure is 5 mm/Hg.

3. The method of producing a modifying agent according to claim 1, wherein each of the hydrolyzable functional groups is selected from the group consisting of an alkoxy group having 1 to 12 carbon atoms, a phenoxy group and a benzyloxy group, or is a halogen atom.

* * * * *